United States Patent [19]

Thir et al.

[11] 4,314,000
[45] Feb. 2, 1982

[54] FIBER LUBRICANTS YIELDING LOW RESIDUES UPON OXIDATION

[75] Inventors: Basil Thir, Grosse Ile, Mich.; David D. Newkirk, Beaverton, Oreg.; Stephen E. Eisenstein, Oak Park; William K. Langdon, Grosse Ile, both of Mich.

[73] Assignee: BASF Wyandotte Corporation, Wyandotte, Mich.

[21] Appl. No.: 203,434

[22] Filed: Nov. 3, 1980

[51] Int. Cl.$^3$ .................. C07C 43/30; C07C 43/32; B05D 3/02; B32B 7/00
[52] U.S. Cl. .............................. 428/265; 427/389.9; 428/267; 428/288; 428/289; 428/278; 568/601; 568/603
[58] Field of Search ............... 427/389.9; 568/601, 568/603; 428/265, 267, 288, 289, 278

[56] References Cited

U.S. PATENT DOCUMENTS

| | | | |
|---|---|---|---|
| 2,786,081 | 3/1957 | Kress | 568/601 |
| 4,111,819 | 9/1978 | Muijs | 427/389.9 X |
| 4,118,326 | 10/1978 | Login | 427/389.9 X |
| 4,189,609 | 2/1980 | Langdon | 568/601 |
| 4,198,464 | 4/1980 | Login et al. | 427/389.9 X |

*Primary Examiner*—Michael R. Lusignan
*Attorney, Agent, or Firm*—H. Lawrence Jones

[57] ABSTRACT

A linked compound is a useful lubricant for fibers such as nylon and polyester, providing low volatility at a temperature below about 230° C. and by oxidizing, leaving a low level of residue, at temperatures above about 230° C.

23 Claims, No Drawings

FIBER LUBRICANTS YIELDING LOW RESIDUES UPON OXIDATION

BACKGROUND OF THE INVENTION

1. Field of the Invention

The present invention relates to the use of a linked compound as a fiber lubricant yielding a very low level of residue when oxidized at high temperatures. More particularly, a compound linked with formal, acetal, ketal and carbonate is useful as a fiber lubricant when applied to a fiber in an amount of from 0.05 weight percent to 5 weight percent, based on the weight of the fiber lubricant, because the lubricant provides less than 10 weight percent loss at a temperature of less than 230° C. and a residue of less than two weight percent, based on the weight of fiber lubricant, after oxidation at a temperature of about 240° C. for 24 hours.

2. Description of the Prior Art

A fiber lubricant formulation consists of a base material such as mineral oil, alkyl esters of fatty acids or vegetable oils, emulsifiers that allow the lubricant to be applied from a water solution, antistatic agents, antioxidants, bacteriocides, friction modifiers or buffering agents.

A fiber lubricant is critical to the conversion of nylon or polyester fiber into useful yarn for textile manufacturing. The fiber lubricant has several functions. One function is to control friction. The fiber lubricant may protect the newly spun fiber from fusion or breakage by controlling the yarn to metal friction at frictional contact points between the yarn and machine guides, rollers, draw plates, heater plate and texturing false twist spindles or friction discs. Another function is to protect the fiber from heat generated at a heater temperature by heater plates or from heat at the frictional contact points. The lubricant also functions to provide for yarn cohesion giving strength to the yarn by holding the yarn bundled together and by allowing the yarn to build up an acceptable package at the end of processing. Static electricity that is formed as the yarn rapidly moves through the processing equipment would also be controlled. The lubricant must also protect machine surfaces from wear.

Synthetic fibers are drawn and textured or bulked to yield optimum physical properties of strength, increased covering, pleasing hand, and greater warmth. During both texturing and bulking, the yarn is exposed to high temperatures such as by passing the fibers through a heating zone. In the heating zone, the fibers are heated to a fiber temperature by a heater plate at a heater plate temperature.

The fiber temperature is within a fixed temperature range within which the fiber will remember an orientation or other imparted characteristic. The fiber lubricant must show acceptable thermal stability in air and should evaporate very little or have low volatility at the fiber temperature.

The heater plate temperature has been increased by the manufacturers in recent years in order to provide faster throughput. Since the fiber temperature is a function of the heater plate temperature and the length of the time in the heating zone, as the speed of the fiber throughput increases, the fiber temperature may be maintained by increasing the heater plate temperature. Increased fiber speed places increased stress on the lubricant to protect the fiber. Increased heater plate temperature places increased demands on the fiber lubricant degradation. It has become increasingly more important that fiber lubricants degrade at high temperatures, such as at the heater plate temperature, in a controlled manner without leaving a residue. The fiber lubricant should evaporate very little at the fiber temperature, but that fiber lubricant which does evaporate should, upon approaching the heater plate temperature, degrade to volatile products leaving a very small residue.

Compounds containing acetal linkages have been disclosed in the prior art as evidenced by U.S. Pat. No. 2,786,081 which discloses polymeric condensation products of polyalkylene glycols and aldehydes. U.S. Pat. No. 4,189,609 makes a very general suggestion to use formal-containing products in textile applications, however, there is no suggestion that formal-containing products would have use as a fiber finish component because of their unique thermal properties.

SUMMARY OF THE INVENTION

It has been discovered that a linked compound is a useful lubricant for polyester and nylon fibers during a drawing and texturing operation. Surprisingly, this class of lubricants yields a very low level of residue at high temperatures.

A process of lubricating synthetic fibers comprises applying to the fiber in an amount of from 0.05 weight percent to 5 weight percent, based on the weight of lubricated fiber, of a linked compound which is of the general formula:

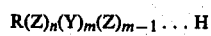

$$R(Z)_n(Y)_m(Z)_{m-1} \ldots H$$

wherein R is HO or an alkoxy group having from 1 to 8 carbons; Z is a linker selected from the group consisting of

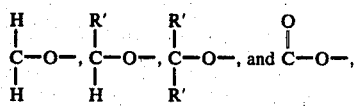

wherein R' is independently selected from methyl, ethyl, propyl, isopropyl or phenyl; Y is a polyoxyalkylene group made up from about 2 to x units wherein each unit is selected individually, in heteric or block mixtures thereof from oxyethylene, oxypropylene, oxybutylene, and oxytetramethylene; x is a number selected such that the approximate average molecular weight contribution of the polyoxyalkylene group is from about 100 to about 800, preferably 106 to about 500, m is a number from 2 to 40, preferably 4 to 6 when Z is

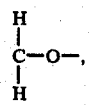

n is 1 or 0, with the proviso that when R is HO, n equals 0, with the further proviso that the Z groups can be coupled to the Y groups either in a heteric or block arrangement and with the further proviso that a unit of Z is not directly attached to the terminal H. Compounds that fall within the range of the above mentioned formula are disclosed in U.S. Pat. Nos. 3,931,337, 4,072,704 and 4,189,609 incorporated by reference herein.

The products of use in the invention are useful fiber lubricants because upon oxidation at high temperatures, a very low residue remains. The products used in this invention evaporate providing a volatility of less than ten weight percent, based on the weight of the fiber lubricant, at a temperature of less than about 230° C. and oxidize, leaving a level of residue of less than two percent based on the weight of fiber lubricant at a temperature greater than about 230° C. These temperatures may be reached at various points in the fiber manufacture, such as at the approach of evaporating lubricant to the heater plate and at the many different frictional contact points of fiber to metal.

DESCRIPTION OF THE PREFERRED EMBODIMENTS

When temperatures greater than about 230° C. occur at locations such as the heater plate, the products of use in this invention will begin volatilizing, and upon approaching the temperature of 250° C., will oxidize to products which leave a residue of less than two weight percent based on the weight of fiber lubricant.

The products of this invention are particularly useful as fiber lubricants for high speed texturing of nylon or polyester. In this application, the balance of the fiber lubricant formulation, which does not evaporate, will show changed frictional properties that allow optimum processability in later stages of the texturing process as, for example, when the yarn contacts the friction discs.

In the preparation of the compounds of use in this invention, four different kinds of linkers can be employed, i.e., formal, acetal, ketal and carbonate linkers.

In the preparation of the formal-linked lubricants of use in this invention, formaldehyde is employed either in the form of paraformaldehyde or a solution of formaldehyde in water, preferably a 37 weight percent solution of formaldehyde in water. The form of the formaldehyde is not critical. The important concept is that the aldehyde be available during the condensation reaction to create a formal bond. Other formaldehyde producing compounds which may be used are trioxane and methylal.

In the preparation of the acetal-linked lubricants of use in this invention, aldehydes of the general formula R'-CHO, wherein R' is methyl, ethyl, propyl, isopropyl or phenyl, such as acetaldehyde, propionaldehyde and butyraldehyde, may be employed.

Used in the preparation of the ketal-linked lubricants of use in this invention, are ketone compounds of the general formula:

wherein each R' is independently selected from methyl, ethyl, propyl, isopropyl, or phenyl, such as butanone, 2-pentanone and 3-pentanone.

Also possibly used are methyl ketones of the general formula:

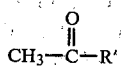

wherein R' is methyl, ethyl, propyl, isopropyl or phenyl.

The carbonate-linked lubricants of use in this invention are prepared from dialkyl carbonates such as diethyl carbonate.

An alkylene glycol used in the preparation of Y in the lubricants of use in this invention include ethylene glycol, propylene glycol, butylene glycol and tetramethylene glycol as well as ethylene oxide, propylene oxide, butylene oxide, and tetrahydrofuran adducts of these glycols. Representative adducts range from diethylene glycol to an approximately 500 molecular weight adduct of ethylene oxide, an approximately 500 molecular weight adduct of propylene oxide with propylene glycol, an approximately 500 molecular weight adduct of butylene oxide with butylene glycol and an approximately 500 molecular weight adduct of tetrahydrofuran with 1,4-butylene glycol. Mixtures of alkylene glycols and of adducts thereof as well as mixtures of glycols and adducts can be used. Overall, the average molecular weight of the glycols and adducts will vary from 106 to about 800, preferably 106 to 500.

The formal lubricants of use in this invention are prepared by the condensation of the formaldehyde and the alkylene glycol at 25° C. to 150° C. in the presence of an acid catalyst. Suitable catalysts are sulfuric acid, hydrochloric acid, hydrobromic acid, p-toluene sulfonic acid, phosphoric acid, trifluoracetic acid, methane sulfonic acid and trichloroacetic acid. The preferred catalyst is sulfuric acid. The amount of catalyst will vary from 0.05 weight percent to 0.6 weight percent, preferably 0.1 weight percent to 0.3 weight percent, based on the total weight of reactants. The molar ratio of the alkylene glycol to the formaldehyde may range from about 1:1 to 2:1.

The condensation reaction is carried out in the presence of a water-immiscible solvent which is employed to remove the water of reaction by an azeotropic distillation. Examples of such solvents are benzene, toluene, xylene, hexane and cyclohexane. The preferred solvent is hexane. The condensation reaction is then refluxed at a temperature of from 25° C. to 150° C., preferably 65° C. to 70° C., for 5 hours to 9 hours or until complete. The crude product is then neutralized with a salt such as sodium carbonate. The solvent is removed by stripping at a temperature of from 140° C. to 150° C. and a pressure of 5 millimeters to 15 millimeters Hg for a time period of about 15 minutes to 1 hour or until the solvent is removed. Upon filtration, the product is complete.

The acetal lubricants of use in this invention may be prepared by a condensation reaction similar to that used for the formal preparation.

The ketal lubricants of use in this invention may be prepared by reacting the methyl ketone or ketone compounds stated above with the alkylene glycol.

The carbonate fiber lubricants of use in this invention are prepared by the reaction of about 0.5 to about 1 mole of alkyl carbonate for every mole of oxyalkylene unit, thus forming an hydroxy-terminated product [compare carbonate-terminated hydroxy compound]. The coupling reaction with the dialkyl carbonate is carried out at a temperature range of about 100° C. to 200° C. in the presence of alkaline catalysts. Examples of such catalysts are sodium carbonate, potassium carbonate, sodium methoxide, sodium ethoxide, potassium methoxide, and potassium ethoxide, sodium hydroxide, potassium hydroxide and mixtures thereof. The preferred alkaline catalyst is potassium carbonate. The amount of catalyst employed may vary from about 0.01 weight percent to about 1 weight percent based on the total weight of reactants. The amount of the alkaline catalysts is not critical, however, it is necessary that the coupling reaction with the dialkyl carbonate occur at an alkaline pH. The pH may vary from 8 to 11, preferably from 8 to 10. The reaction with dialkyl carbonate occurs as the result of an ester interchange. As the temperatures raise from 100° C. to 200° C., an alkanol is distilled off resulting in the ester interchange. This results in the coupling of oxyalkylene groups with the carbonate groups.

The products used in this invention are applied to fibers, preferably a nylon or polyester fiber, in an amount of from 0.05 weight percent to 5 weight percent, preferably 0.5 weight percent to 1.5 weight percent, based on the weight of the lubricated fiber and have an average molecular weight of about 200 to about 33000, preferably about 500 to about 1500. A formal condensation product is used in this invention in the amount of 0.05 weight percent to 5 weight percent, preferably 0.5 weight percent to 1.5 weight percent and has a molecular weight range of about 200 to about 2000 preferably about 500 to about 1500.

In an embodiment of the invention, the formal condensation product of formaldehyde and diethylene glycol of an average approximate molecular weight of 550 to 750 is used in an amount of 0.5 weight percent to 1.5 weight percent based on the weight of lubricated fiber, such as nylon or polyester fiber.

In another embodiment of the invention, the formal condensation product of dipropylene glycol and formaldehyde of an approximate average molecular weight of 750 to 800 is used in amounts of from 0.5 weight percent to 1.5 weight percent based on the weight of lubricated fiber, such as nylon or polyester fiber.

Also used is the formal condensation product of formaldehyde and a mixture of equal parts by weight of a polyoxypropylene adduct of propylene glycol of approximate average molecular weight of 425 and a polyoxyethylene adduct of ethylene glycol of approximate average molecular weight of 200 in a total amount of 0.5 weight percent to 1.5 weight percent based on the weight of the lubricated fiber, such as nylon or polyester fiber.

The product used in this invention will yield volatile products such that a weight loss of less than 10 weight percent based on the weight of fiber lubricant is observed at a temperature of less than 230° C. At temperatures of less than 230° C., the product of Example 1, of use in this invention, will provide a volatility of a weight loss of less than five weight percent based on the weight of fiber lubricant.

The products used in this invention will oxidize in a controlled manner at temperatures between 220° C. and 250° C. and above to leave a very low residue build up. The products contain only limited volatile material that is lost below 220° C.-250° C. Above the range 220° C.-250° C. the product oxidizes to products that are volatile and thus form minimal solid residues. At a temperature of 240° C., after oxidation for 24 hours, the product of Example 1 of use in this invention left a residue of less than 1.0 weight percent based on the weight of fiber lubricant; the product of Examples 2 and 3 of use in this invention left a residue of less than 0.7 weight percent based on the weight of fiber lubricant, and the product of Example 4 of use in this invention left a residue of less than two weight percent based on the weight of fiber lubricant.

There is the additional advantage that the formal linkages in the formal condensation product used in this invention should rapidly degrade in the environment, such as in waste treatment ponds, with properly selected, slightly acidic pH.

The following examples will further illustrate the various aspects of the invention. Where not otherwise specified throughout this specification and claims, temperatures are in degrees centigrade, and parts, percentages and proportions are by weight.

EXAMPLE 1

To a clean, dry round-bottom flask equipped with a stirrer, reflux condenser, Dean Starke water separator, thermometer and nitrogen inlet was charged:

|  | Parts |
|---|---|
| Polyoxypropylene adduct of propylene glycol of approximate average molecular weight of 425 | 330 |
| Polyoxyethylene adduct of ethylene glycol of approximate average molecular weight of 200 | 330 |
| 37% Aqueous solution of formaldehyde | 220 milliliters |
| Hexane | 200 milliliters |
| Sulfuric acid | 1 |

The reaction mixture was refluxed at 70° C. for 7.5 hours while water was collected. The crude product was neutralized with sodium carbonate and left standing overnight. The hexane was stripped off at 150° C., 10 millimeters Hg, for thirty minutes, and then filtered to yield 669 parts of product.

EXAMPLE 2

The procedure of Example 1 was generally followed to react the following:

|  | Parts |
|---|---|
| Diethylene glycol | 318 |
| Formaldehyde as paraformaldehyde | 70 |
| Hexane | 200 milliliters |
| Sulfuric acid | 1 |

The reaction mixture was refluxed at 70° C. for about 6 hours until 29.9 parts of water were collected. The neutralized product was then separated from hexane by distillation followed by 30 minutes of vacuum stripping at 140° C., 10 millimeters Hg pressure. Filtration yielded 340 parts of product.

EXAMPLE 3

The procedure of Example 1 was generally followed to react the following:

|  | Parts |
|---|---|
| Diethylene glycol | 721 |
| 37% Aqueous solution of formaldehyde | 520 milliliters |
| Hexane | 150 milliliters |
| Sulfuric acid | 1.5 milliliters |

The reaction mixture was refluxed at 65° C. for about 7 hours until all water was removed. The neutralized product was then separated from the solvent by distillation and vacuum stripping at 140° C. to 150° C. for one hour. Filtration yielded 740 grams product.

EXAMPLE 4

The procedure of Example 1 was generally followed to react the following:

|  | Parts |
| --- | --- |
| Dipropylene glycol | 844 |
| Formaldehyde as paraformaldehyde | 162 |
| Hexane | 300 milliliters |
| Sulfuric acid | 1.5 milliliters |

The reaction mixture was refluxed at 70° C. for 8 hours. After standing overnight, the product was heated to remove the hexane and any remaining water. After neutralization, the product was filtered then considered complete.

Thermogravimetric weight loss data was obtained for Examples 1 and 2 of the invention. The temperatures in degrees Centigrade at which one percent, five percent and ten percent of the weight of the product was lost are presented below in Table 1 for air and nitrogen atmospheres.

TABLE 1

| Temperature at | Example 1 | Example 2 |
| --- | --- | --- |
| 1% Weight Loss - Air (°C.) | 209 | 171 |
| 1% Weight Loss - $N_2$ (°C.) | 224 | 191 |
| 5% Weight Loss - Air (°C.) | 236 | 201 |
| 5% Weight Loss - $N_2$ (°C.) | 272 | 242 |
| 10% Weight Loss - Air (°C.) | 255 | 233 |
| 10% Weight Loss - $N_2$ (°C.) | 304 | 296 |

Examples 3 and 4 were not run for thermogravimetric weight loss. Both examples of the invention show low volatility, less than 10 percent, in the temperature range of 210° to 230° C.

Physical and thermal properties were run on Examples 1-4 and the results are shown in Table 2 below. Also shown in Table 2 below are results of a test to provide the percent residue after prolonged heat at 240° C. Metal cups, three for each example, were placed on a heater and maintained at 240° C. for 24 hours. At intervals of time, the weight loss for each of the three samples was determined and averaged. Those results are shown below in Table 2.

TABLE 2

| Physical & Thermal Properties | 1 | 2 | 3 | 4 |
| --- | --- | --- | --- | --- |
| Thin film smoke point | 175 | 159 | 166 | 125 |
| Cloud point, 1% aqueous solution (°C.) | 44 | 100 | >100 | insoluble |
| Brookfield viscosity (cps) | 530 | 280 | 304 | 640 |
| SUS viscosity (SUS) | 958 | 551 | 662 | 705 |
| Molecular weight based on OH number | 1486 | 550 | 715 | 782 |
| Percent residue after prolonged heating at 240° C., % | | | | |
| 0.5 hour | 65.6 | 44.6 | 33.4 | 82.8 |
| 1.0 hour | 21.6 | 11.0 | 1.3 | 71.3 |
| 2.0 hours | 3.7 | 2.6 | 0.7 | 55.8 |
| 4.0 hours | 1.7 | 0.7 | 0.4 | 13.8 |
| 6.0 hours | 1.5 | 0.7 | 0.4 | 3.0 |
| 24 hours | 0.9 | 0.6 | 0.4 | 1.7 |
| Final Appearance of Residue | Varnish | Varnish | Varnish | White Solid |

The embodiments of the invention in which an exclusive privilege or property is claimed are defined as follows:

1. A process of lubricating synthetic fibers which comprises applying to the fiber in an amount of from 0.05 weight percent to 5 weight percent, based on the weight of lubricated fiber, of a compound of the general formula:

$$R(Z)_n(Y)_m(Z)_{m-1} \ldots H$$

wherein R is HO or an alkoxy group having from 1 to 8 carbons in the alkyl chain; Z is a linker selected from the group consisting of

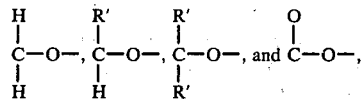

wherein each R' is independently selected from methyl, ethyl, propyl, isopropyl or phenyl; Y is a polyoxyalkylene group made up from about 2 to x units wherein each unit is selected individually, in heteric or block mixtures thereof from oxyethylene, oxypropylene, oxybutylene, and oxytetramethylene; x is a number selected such that the approximate average molecular weight contribution of the polyoxyalkylene group is from about 100 to about 800; m is a number from 2 to 40; n is 1 or 0, with the proviso that when R is HO, n equals 0, with the further proviso that the Z groups can be coupled to the Y groups either in a heteric or block arrangement, and with the proviso that a unit of Z is not directly attached to the terminal H.

2. The process of claim 1 which further comprises heating the fiber which has been lubricated with the fiber lubricant described in claim 1 whereby a volatility at temperature less than 230° C. is less than 10 weight percent loss based on the weight of the fiber lubricant, and a residue is less than two weight percent based on the weight of fiber lubricant after oxidation at a temperature of about 240° C. for 24 hours.

3. The process of claim 1 wherein Z is

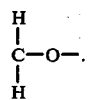

4. The process of claim 1 wherein Z is

wherein R' is selected from the group methyl, ethyl, propyl, isopropyl or phenyl.

5. The process of claim 1 wherein Z is

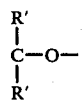

wherein each R' is independently selected from the group methyl, ethyl, propyl, isopropyl or phenyl.

6. The process of claim 1 wherein Z is

7. The process of claim 3 which further comprises heating the fiber which has been lubricated with the fiber lubricant described in claim 1 whereby a volatility at temperatures less than 230° C. is less than 10 weight percent loss based on the weight of the fiber lubricant and the residue is less than 2 weight percent based on the weight of fiber lubricant after oxidation at a temperature of about 240° C. for 24 hours.

8. The process of claim 3 in which the fiber lubricant is the condensation product of diethylene glycol and formaldehyde with an approximate average molecular weight of the condensation product of from 500 to 750.

9. The process of claim 7 in which the fiber lubricant is the condensation product of diethylene glycol and formaldehyde of an approximate average molecular weight of condensation product from 500 to 750.

10. The process of claim 9 in which the residue is less than 0.7 weight percent based on the weight of fiber lubricant after oxidation at a temperature of about 240° C. for 24 hours.

11. The process of claim 3 in which the fiber lubricant is the condensation product of formaldehyde and a mixture of equal parts by weight of a polyoxypropylene adduct of propylene glycol of approximate average molecular weight of 425 and a polyoxyethylene adduct of ethylene glycol of approximate average molecular weight of 200 with an overall approximate average molecular weight of condensation product from 1000 to 2000.

12. The process of claim 7 in which the fiber lubricant is the condensation product of formaldehyde and equal parts of a polyoxypropylene adduct of propylene glycol of approximate average molecular weight of 425 and a polyoxyethylene adduct of ethylene glycol of approximate average molecular weight of 200 with an overall approximate average molecular weight of condensation product from 1000 to 2000.

13. The process of claim 12 in which the residue is less than 1.0 weight percent based on the weight of fiber lubricant after oxidation at a temperature of about 240° C. for 24 hours.

14. The process of claim 12 in which less than five weight percent based on the weight of fiber lubricant is lost at fiber temperatures of less than 230° C.

15. A nylon or polyester fiber coated with a fiber lubricant comprising a condensation product of formaldehyde and an alkylene glycol, an alkylene oxide adduct thereof, and mixtures thereof, in which the alkylene radicals contain from 2 to 3 carbon atoms, said condensation product being present in an amount of from 0.05 weight percent to 5 weight percent based on the weight of lubricated fiber and such lubricant showing a volatility at a temperature of approximately 230° C. below 10 weight percent loss based on the weight of fiber lubricant and yielding a level of residue of less than two weight percent based on the weight of the fiber lubricant upon oxidation at the heater plate temperature.

16. The fiber of claim 15 wherein said fiber is a textile fiber.

17. The fiber of claim 16 wherein the textile fiber is a polyester.

18. The fiber of claim 17 wherein the polyester is poly(ethylene terephthalate).

19. The fiber of claim 16 wherein the textile fiber is nylon.

20. The process of claim 4 wherein R' is methyl.

21. The process of claim 5 wherein each R' is methyl.

22. The process of claim 5 wherein one R' is methyl and the other R' is ethyl.

23. The process of claim 5 wherein each R' is ethyl.

* * * * *